US00PP07961P

United States Patent [19]

Millon et al.

[11] Patent Number: Plant 7,961

[45] Date of Patent: Sep. 1, 1992

[54] GUZMANIA "LEMONADE"

[76] Inventors: David P. Millon; Beth L. Millon, both of 21975 SW. 147 Ave., Goulds, Fla. 33170

[21] Appl. No.: 671,210

[22] Filed: Mar. 18, 1991

[51] Int. Cl.[5] ..... A01H 5/00

[52] U.S. Cl. ..... Plt./88.6

[58] Field of Search ..... Plt./88, 88.1, 88.8

*Primary Examiner*—Howard J. Locker

[57] ABSTRACT

Guzmanis 'Lemonade' is a bromeliad characterized by long strap-like glossy leaves that form a rosette at the center of which is a tall showy bloom spike. This inflorescence is a bright and vivid yellow, often with traces of red and orange. These colors set Guzmania 'Lemonade' apart from any known cultiver of the Guzmania genus. The inflorescence of Guzmania 'Lemonade' will last between 3 and 6 months under most conditions. The Guzmania 'Lemonade' is especially suited to use as an interior houseplant as it will tolerate a wide variety of environmental conditions.

5 Drawing Sheets

The present invention relates to a new cultivar of the genus Guzmania of the family Bromeliacea. The cultivars of Guzmania are very showy plants, comprised of normally green leaves growing in a rosette form, at the center of which are generally spiked shaped bracts which form a large upright inflorescence bearing tubular shaped flowers. The cultivars have usually been named after their bract color.

The new cultivar was discovered by the applicant in 1988 as a sport of Guzmania 'Cherry' (not patented). The sports occurred in the greenhouses owned by the applicant in Goulds, Fla. The distinction of a new cultivar was recognized by the striking yellow color of the inflorescence, significantly different than any other known Guzmania hybrids. The newly discovered sport is similar in many respects to the characteristics of the cultivar Guzmania 'Cherry' in its compact growth habit, deep green foliage, and relative ease of cultivation. Asexual propagation by means of stem cuttings as performed in Goulds, Fla. has demonstrated that the combination of characteristics herein disclosed are faithfully reproduced in succeeding generations and appear to be firmly fixed. Guzmania 'Lemonade' has not been observed under all possible environmental conditions as it only exists in the greenhouses of the applicant. The phenotype may vary with differences in culture, environment and growing conditions. The following descriptions apply to the existing plants grown under the shadehouse conditions in Goulds, Fla.

The accompanying photographic drawings show typical inflorescence and foliage characteristics of Guzmania 'Lemonade'. Sheet 1 shows a potted specimen that is approximately 17 months old from initial propagation of a 8 week old offshoot.

Sheet 2 shows a close-up of the inflorescence at an early stage of development.

Sheet 3 shows the inflorescence approaching maturity.

Sheets 4 and 5 show 2 different views of the flower that is borne on a mature inflorescence.

The following color notations were derived by comparison with the color specimens in "The Munsell Book of Color" glossy edition, published by the Munsell Color Company, Inc. of Baltimore, Md. The following description is based upon plants that were 16–18 months old from offshoots and were then grown in approximately 85% shaded conditions in Goulds, Fla. The temperature range was from 75 to 105 degrees F. during the summer, and from 40 to 90 degrees F. during the winter months.

PLANT

The diameter of a fully grown Guzmania 'Lemonade' is approximately 80 cm. The height of the plant, including the flower bracts and flowers, is approximately 70 cm. The height of the foliage is approximately 50 cm.

LEAVES

The leaves are medium to dark green, the same color appearing throughout the foliage. The adaxial side of the leaves are green-yellow (10 GY 3/4) and the abaxial side of the leaves are green-yellow (5 GY 3/4). The most basal leaves are the largest, approximately 50 cm. long. These leaves are about 6 cm. wide at the base of the rosette, becoming 4 cm. wide within 5 to 6 cm. of the rosette. The width of the leaf continues approximately 4 cm. for the majority of its length, then tapering to a ½ cm. apex during the distel 5 cm. portion of the leaf. Each emerging leaf is gradually shorter than the last, with emerging leaf length gradually being reduced until the 6 to 7 cm. long bract is produced. The plant normally produces 25 to 30 leaves before inflorescence.

BRACTS

The bracts are generally spike shaped, collectively forming a main sword with a star shaped cross section (when viewed from above), which can extend from the center of a mature plant approximately 45 cm. above the leaves, and forming a very striking contrast with the leaves. Approximately 25 individual bracts form the main inflorescence. The overall width of the inflorescence is approximately 15 to 18 cm. The bracts are approximately 5 cm. wide at the base, gradually tapering acicularly along their 6 to 7 cm. length, terminating acuminate fashion. The predominant color of the main inflorescence is yellow (5 Y 7/10). The basal portion of the bracts have yellow-green hue corresponding to (10 Y 5/8). Bracts that are lower than approximately #8 (counting from the top) commonly have an increasing amount of red (7.5 R 2/8) and (7.5 R 3/8) appearing on the distal portion of the bracts. This color ranges from an intense red at the tip and growing less distinct towards the basal portion of the bract, merging with the overall yellow (5 Y 7/10) of the bract. This red tip may range from non existent to 3 cm. wide. Beginning with approximately bract #15 (counting from the top) there may occur an increasing amount of green (10 GY 3/4) and (5 GY 3/4) that replaces the basal portion of the red (7.5 R 2/8) and (7.5 R 3/8) that may appear on the lower bracts usually #8 through #15. This green (10 GY 3/4) increases in width both towards the distal and basal portions of the bracts, finally eclipsing all traces of the yellow (5 Y 7/10) and red (7.5 R 3/8) and (7.5 R 2/8) as the bracts merge with the main body of the plant. The adaxial and abaxial sides of the bracts are usually similar to each other in color. Occasionally the abaxial sides of the lower bracts (#15 to #25 from the top) have an increasing amount of orange (7.5 R 4/8) that replaces or blends in with the green (5 GY 3/4) and (10 GY 3/4), yellow (10 Y 5/8) and red (7.5 R 2/8) and (7.5 R 3/8). The inflorescence will hold its color for between 3 and 6 months.

FLOWERS

The flowers are generally tubular shaped and the visible portion is orange (10 YR 8/14) at the distal end. The mid area, which is not visible without dissection, is yellow (5 Y 8.5/6) and the basal area is yellow (7.5 Y 8.5/4). The flowers are located in tight groups of approximatrely 10 flowers and are found at the junction of the bracts and main inflorescence. The group of flowers and surrounding sepals, form a calyx that is approximately 6 cm. to 8 cm. long and has a maximum diameter of approximately 2 cm. to 3 cm. wide. The calyx has a overall color range of yellow (10 Y 7/8) at the basal third, passing through yellow (7.5 Y 8/6) at the midpoint, and at the distal third the color is yellow (5 Y 8/14). Individual sepals have a length ranging from 4 cm. to 8 cm. and an unfolded width of approximately 5 mm. to 10 mm. The color range is; distal third is yellow (5 Y 8/14), the middle third is yellow (7.5 Y 8/4), and the basal third is yellow (10 Y 9/2). The flowers usually appear at a rate of one per day per group. The flowers rise above the distal end of the calyx approximately 5 mm. above the calyx. The withered flowers disappear back down within the calyx. The flowers are approximately 8 cm. long at maturity. The stamens rise approximately to the level of the pistil which may rise as far as 5 mm. above the flower, however, the pistil and stamens commonly remain with the flower structure.

I claim:

1. A new and distinct cultivar of Guzmania plant named 'Lemonade', as illustrated and described herein.

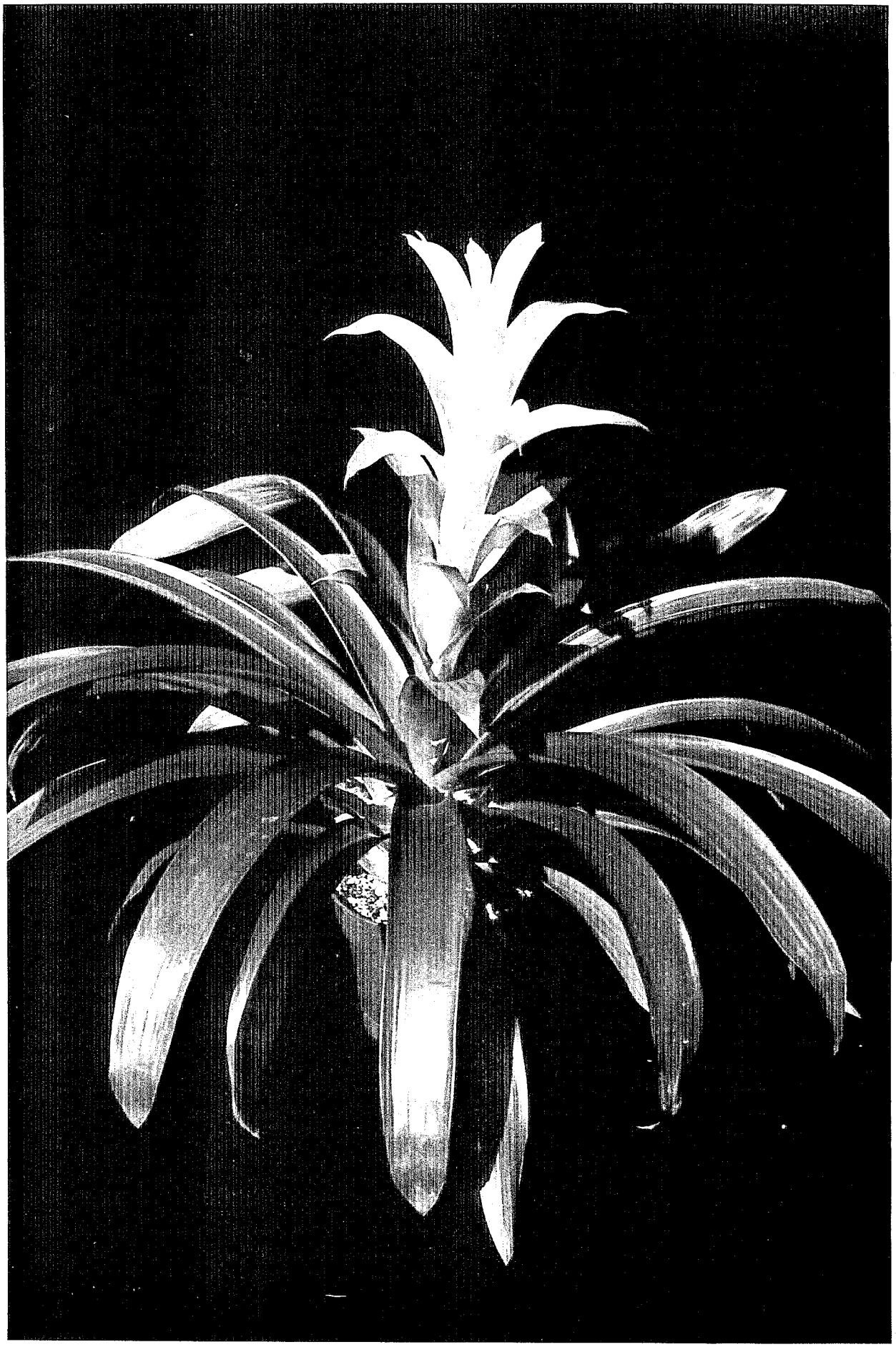

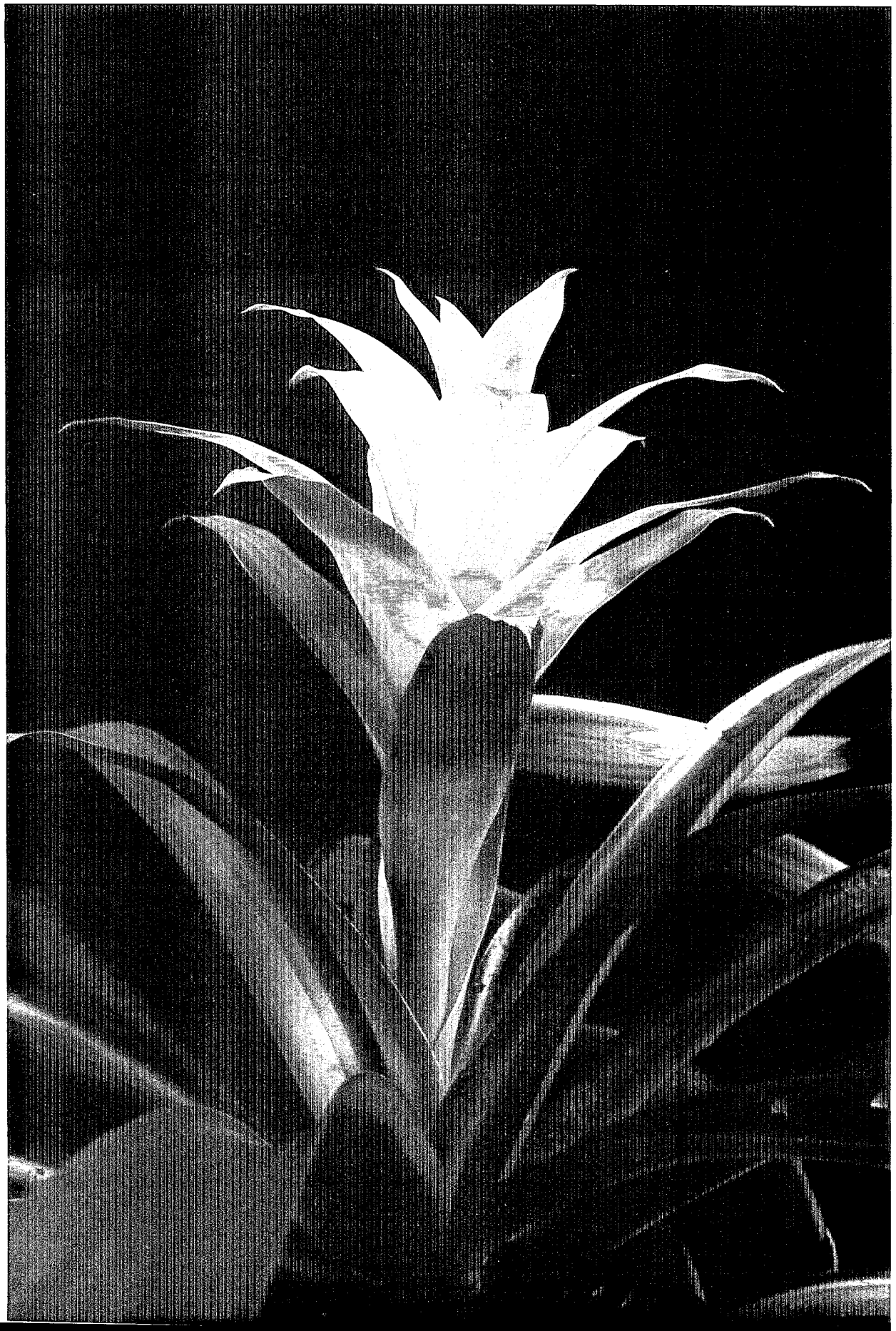

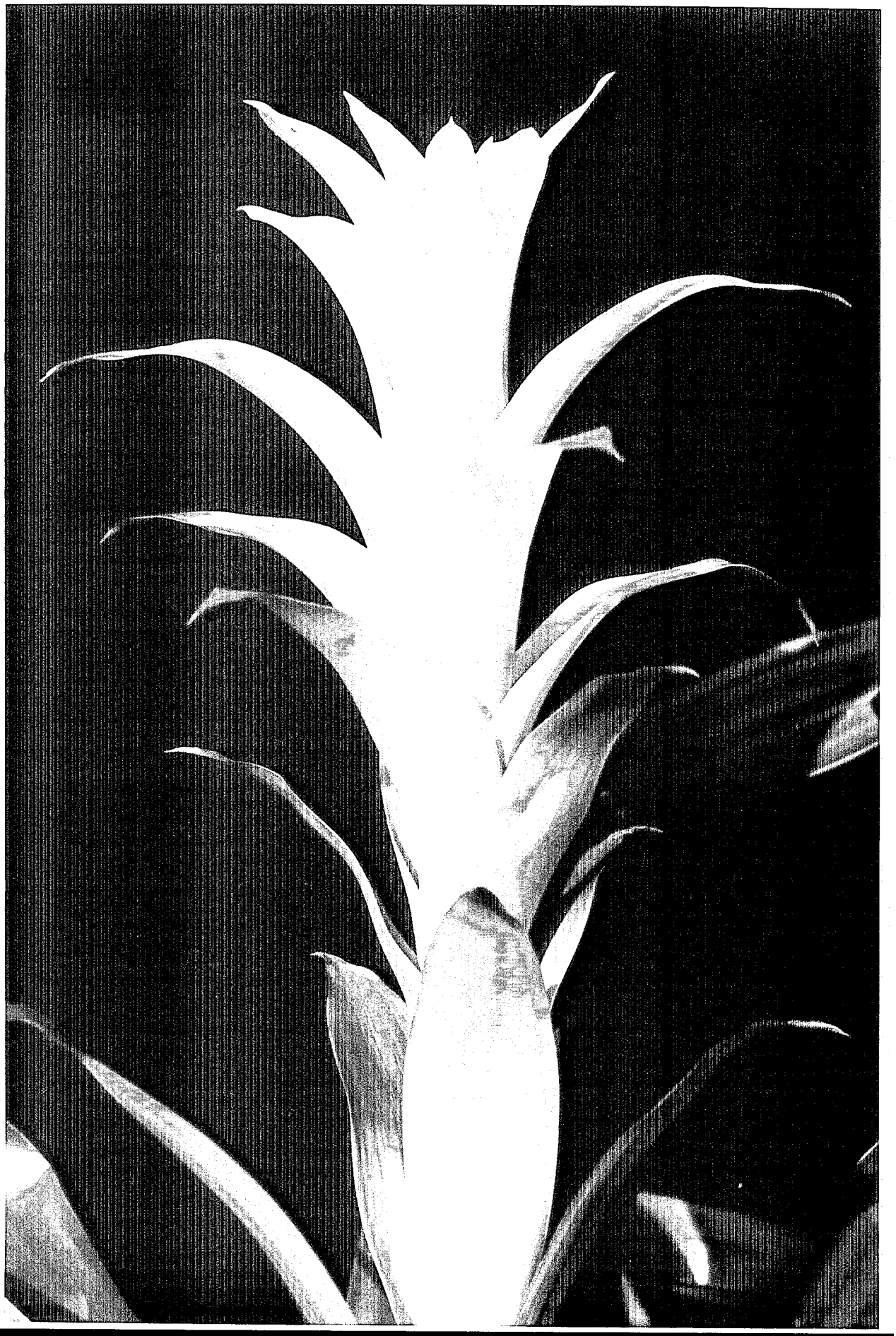

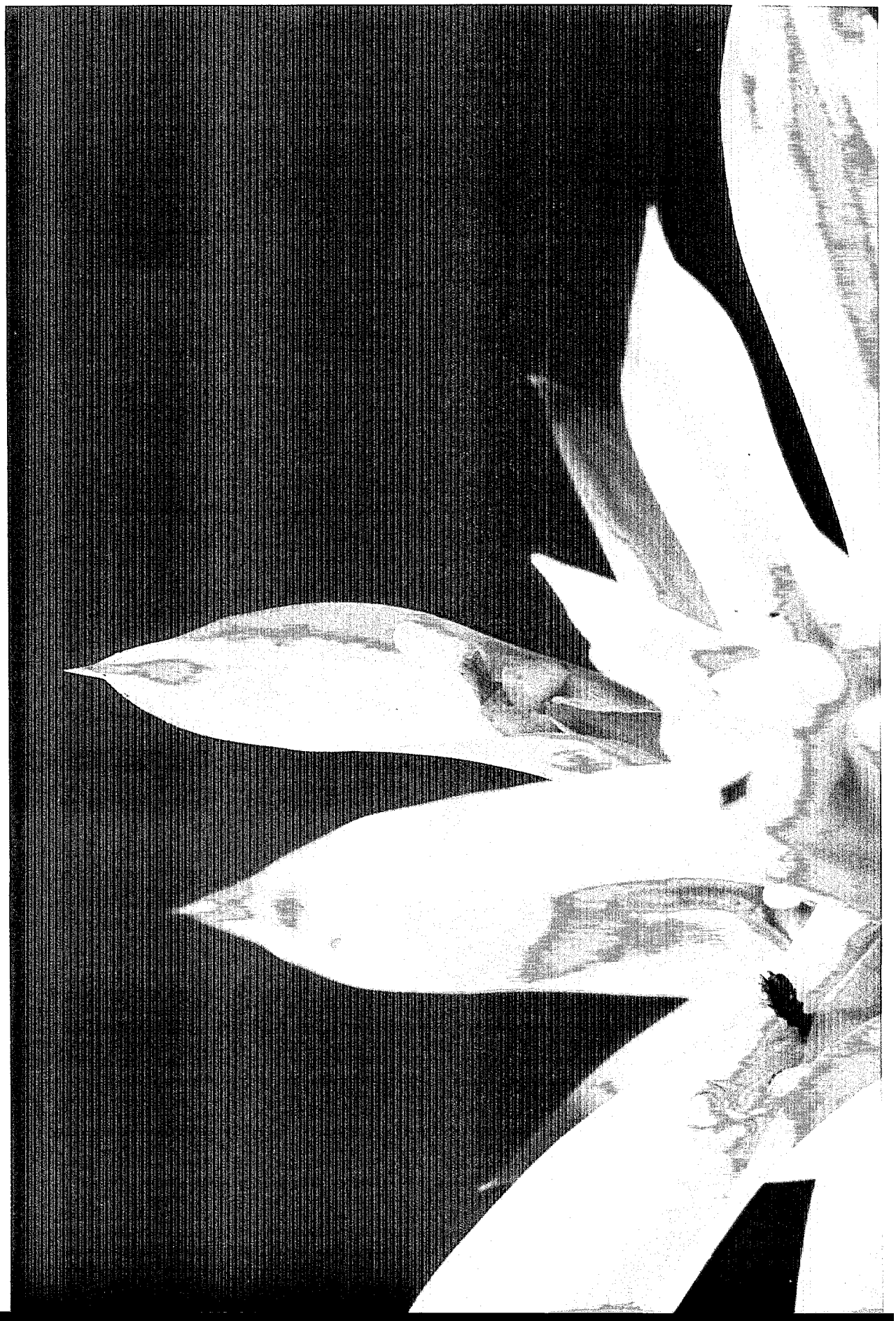

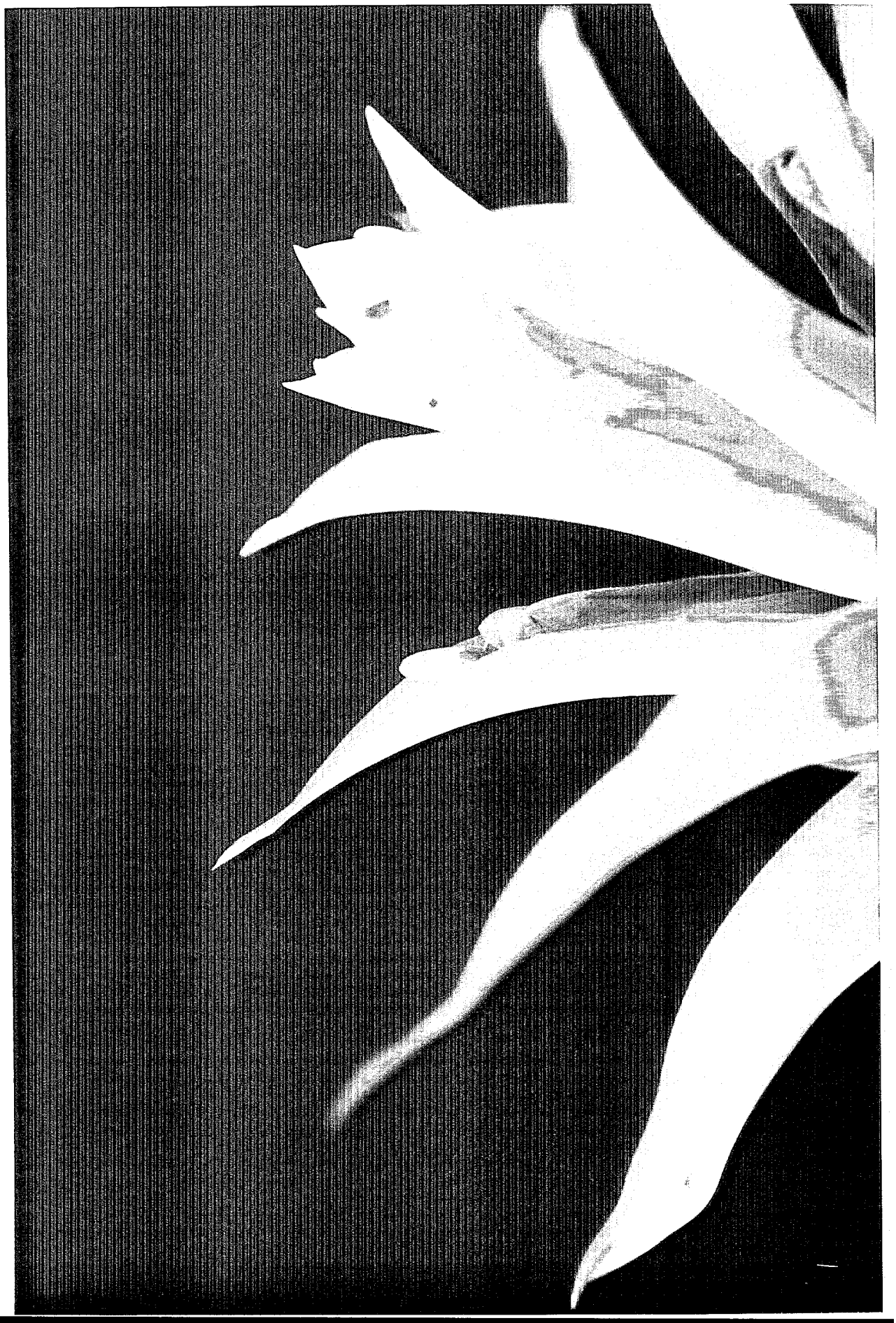

* * * * *